United States Patent [19]

Maulding

[11] Patent Number: 4,675,432

[45] Date of Patent: Jun. 23, 1987

[54] METHOD FOR THE PREPARATION OF ANILINOFUMARATE

[75] Inventor: Donald R. Maulding, Somerville, N.J.

[73] Assignee: American Cyanamid Company, Stamford, Conn.

[21] Appl. No.: 902,274

[22] Filed: Aug. 29, 1986

[51] Int. Cl.$^4$ .......................................... C07C 101/453
[52] U.S. Cl. ...................................... 560/44; 546/170
[58] Field of Search ........................... 560/44; 546/170

[56] References Cited

U.S. PATENT DOCUMENTS

| 3,929,432 | 11/1976 | Napier . | |
|---|---|---|---|
| 4,459,409 | 7/1984 | Ladner | 546/170 |
| 4,476,132 | 10/1984 | Göschke et al. | 560/44 |
| 4,518,780 | 5/1985 | Barton et al. | 546/167 |

Primary Examiner—Natalie Trousof
Assistant Examiner—Bruce D. Gray
Attorney, Agent, or Firm—Estelle J. Tsevdos

[57] ABSTRACT

The present invention relates to methods for the preparation of anilinofumarate, a useful intermediate in the preparation of quinoline-2,3-dicarboxylic acid and in the preparation of 2-(2-imidazolin-z-yl) quinoline-3-carboxylic acid herbicidal agents.

9 Claims, No Drawings

METHOD FOR THE PREPARATION OF ANILINOFUMARATE

BACKGROUND OF THE INVENTION

The present invention relates to novel methods for preparing quinoline-2,3-dicarboxylic acids. These acids are useful intermediates in the preparation of herbicidal pyridine and quinoline imidazolinone herbicidal compounds.

The herbicidal pyridine and quinoline imidazolinone compounds prepared from the present compounds include 2-(4-isopropyl-4-methyl-5-oxo-2-imidazolin-2-yl)quinoline-3-carboxylic acid, and esters and salts thereof and are disclosed in European Patent Application 0 041 623, incorporated herein by reference. These herbicidal imidazolinyl quinolinecarboxylic acids may be prepared by the procedure described in U.S. Pat. No. 4,518,780 (incorporated herein by reference) by cyclization, under basic conditions, with an appropriately substituted 2-carbamoyl quinoline-3-carboxylic acid, that, in turn, is prepared by the reaction of a substituted quinoline-2,3-dicarboxylic acid anhydride and appropriately substituted aminocarboxamide or aminothiocarboxamide. Quinoline-2,3-dicarboxylic acid anhydrides are readily prepared from the diacids by procedures well known in the art. However, the diacids themselves are not readily available.

Pending application for U.S. Letters Patent of Robert Doehner, Ser. No. 698,192 filed Feb. 4, 1985 (incorporated herein by reference) describes a method useful for the preparation of quinoline-2,3-dicarboxylic acid and esters thereof by reacting a beta-anilino-alpha,beta-unsaturated ester with an immonium salt (commonly called a Vilsmeier reagent). The beta-anilino-alpha,beta-unsaturated esters are obtained by the reaction of appropriately substituted anilines with keto-esters or dialkyl acetylene dicarboxylates. This overall reaction for the preparation of quinoline-2,3-dicarboxylates is illustrated in Flow Diagram I.

FLOW DIAGRAM I

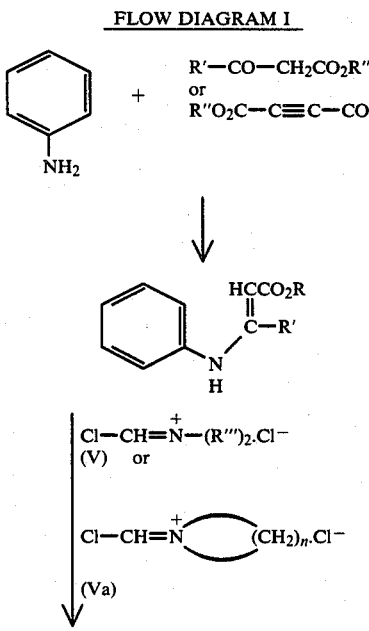

-continued
FLOW DIAGRAM I

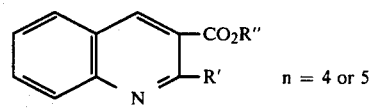

$n = 4$ or $5$ wherein $R'$ is $CH_3$ or $CO_2R''$ and $R''$ is $C_1-C_4$ alkyl, and $R'''$ is $CH_3$ or $C_1-C_4$ alkyl).

When $R'$ is $CH_3$, the diacid is obtained by concurrent oxidation and hydrolysis of the product under aqueous basic conditions in the presence of nickel peroxide, as described in U.S. Pat. No. 4,459,409 (incorporated herein by reference).

Unfortunately, the availability of ketoesters and dialkyl acetylene dicarboxylates, such as diethyloxalacetate and diethyl acetylenedicarboxylate, is limited, thus restricting the quantitites of anilino-fumarate and quinoline-2,3-dicarboxylic acid, the intermediate required for preparing herbicidal 2-(4-isopropyl-4-methyl-5-oxo-2-imidazolin-2-yl)quinoline-3-carboxylic acid, esters and salts thereof.

Co-pending Application for U.S. Letters Patent of D. Maulding, Ser. No. 06/902,275, filed concurrently herewith and incorporated herein by reference describes a method for the preparation of anilinofumarate by the reaction of dichlorosuccinates with specified amines and the subsequent displacement of the amine with aniline in the presence of an organic acid.

SUMMARY OF THE INVENTION

The present invention overcomes not only the limitations of providing a readily-available source of quinoline-2,3-dicarboxylic acid, esters and salts thereof to form anilinofumarate, but the present invention provides for an improvement in reacting dichlorosuccinate with aniline and yielding better results.

Therefore, it is an object of the present invention to provide a novel method for the preparation of anilinofumarate utilizing dichlorosuccinates, obtainable from dialkyl maleates. Since these are readily available in large quantities, an improved method for the manufacture of large quantities of quinoline-2,3-dicarboxylic acid and esters thereof and subsequent production of herbicidal 2-(4-isopropyl-4-methyl-5-oxo-2-imidazolin-2-yl)-quinoline-3-carboxylic acid, esters and salts is provided herein.

Another object of the present invention is to provide a ready source of anilinofumarates as intermediates for the formation of quinoline-2,3-dicarboxylic acids, precursors of the herbicidal agents, 2-(4-isopropyl-4-methyl-5-oxo-2-imidazolin-2-yl)quinoline-3-carboxylic acid, esters and salts thereof by reacting a dichlorosuccinate with an aniline in an inert organic solvent and aqueous base containing a phase transfer catalyst.

These and other objects of the invention are more apparent by reviewing the detailed description provided hereinbelow.

DETAILED DESCRIPTION OF THE INVENTION

The present invention relates to novel methods for preparing anilinofumarates and quinoline-2,3-dicarboxylic acids and esters thereof. These methods comprise reacting a dichlorosuccinate (formula I)

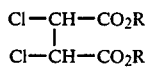
(I)

with a molar equivalent of aniline and a minimum of 2 molar equivalents (equal to or greater than 2 molar equivalents) of aqueous base in the presence of a phase transfer catalyst in an organic solvent at a temperature of about 20° C. to 90° C. for about 1 to 24 hours, and isolating the thus-formed anilinofumarate.

Quinoline-2,3-dicarboxylate acid is then prepared from the thus-formed anilinofumarate by reacting the anilinofumarate with an approximately equimolar amount of a Vilsmeier reagent (immonium salt) in the presence of a hydrocarbon solvent, such as toluene, or a chlorinated hydrocarbon solvent such as methylene chloride, dichloroethane, ortho dichlorobenzene, chlorobenzene, or mixtures thereof, at a temperature of about 40' C. and 110° C., for a period of time sufficient to essentially complete the reaction and yield a dialkyl quinoline-2,3-dicarboxylate. This quinoline-2,3-dicarboxylate is hydrolyzed, under either acid or basic conditions, to give quinoline-2,3-dicarboxylic acid. This procedure is described in co-pending Application for U.S. Letters Patent of R. Doehner, Ser. No. 698,192, filed Feb. 4, 1985, incorporated herein by reference thereto.

The above reactions are graphically illustrated in Flow Diagrams IIa-b.

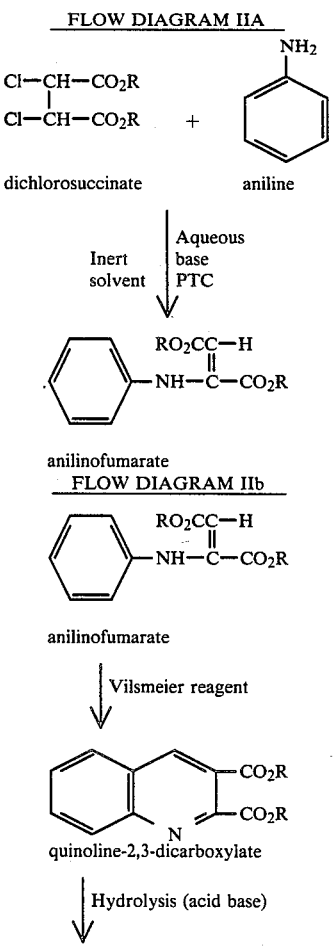

-continued

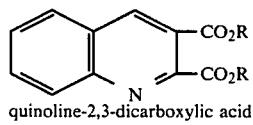
quinoline-2,3-dicarboxylic acid wherein R is as described in formula I.

Surprisingly, it has been found that aniline may be reacted with dialkyl dichlorosuccinates by the method of this invention to directly yield anilinofumarate. This procedure eliminates a processing step required in the recently-discovered novel synthesis of anilinofumarate that first reacts dialkyl dichlorosuccinate with a primary or secondary amine and then reacts the resulting product mixture with aniline, co-pending Application for U.S. Letters Patent of D. Maulding filed concurrently herewith.

The novel method of the present invention thus provides a simple and more direct method for the production of anilinofumarate. This method, in turn, reduces handling, processing, effluent and exposure to intermediate reactions and reagents, resulting in a process that is cleaner, safer, cheaper and more efficient than prior reported methods.

In accordance with the method of this invention, diethyl dichlorosuccinate (0.01 mol), is prepared by the methods described in Japanese Pat. No. 71 21,564 (incorporated herein by reference thereto). In that method, monochlorobenzene is reacted with aniline (0.01 mol) by stirring the mixture in the presence of 0.3 molar equivalents of aqueous sodium hydroxide (33% NaOH w/w) and a catalytic amount (5 mol %) of tetrabutylammonium chloride at 75° C.-80° C. for 2 hours and 30 minutes. The thus-formed anilinofumarate is readily isolated by adding water, washing the organic layer, separating off the organic phase and removing the solvent.

Aqueous bases suitable for the preparation of anilinofumarate by the present method include sodium and potassium hydroxide, at concentrations of 15% to 50% by weight, in amounts of about molar equivalents equal to or greater than 2 molar equivalents, with 3 molar equivalents being preferred.

Quaternary ammonium phase transfer catalysts, such as tetrabutylammonium chloride and benzyltriethylammonium chloride, in amounts as little as 0.05 molar equivalents, have demonstrated comparable results for the method of this invention. Other reagents capable of catalyzing two phase reactions and exhibiting stability under the conditions of this reaction are equally suitable.

Generally, the organic solvents which find utility in the method of the present invention are inert to the reaction conditions and include such solvents as hydrocarbons, aromatic hydrocarbons and chlorinated derivatives thereof, with chlorinated aromatic hydrocarbons, such as chlorobenzene, and aromatic solvents, such as toluene, being preferred.

The reaction of the invention proceeds at varying rates at a temperature range of about 20° C. to 90° C., with 20° C. to 85° C. being preferred, 20° C. to 80° C. most preferred.

The method of the present invention is further illustrated by the following non-limiting examples.

EXAMPLE 1

Preparation of dichlorosuccinate

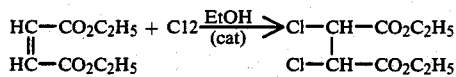

Chlorine gas is bubbled into an ethylene dichloride solution of diethyl maleate containing ethanol, (0.1 molar equivalents). After stirring the mixture at room temperature for 8 hours, it is flushed with nitrogen gas for 5 minutes and the solvent removed under reduced pressure to yield the dichlorosuccinate in 94% yield.

EXAMPLE 2-6

Preparation of diethyl anilinofumarate

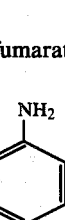
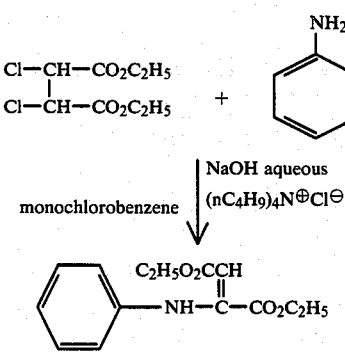

Aniline (0.93 g, 0.01 mol) is added to a stirred solution of diethyl dichlorosuccinate (prepared as described in example 1 above from diethyl maleate (0.01 mol) in monochlorobenzene). Aqueous sodium hydroxide (3.6 g, 33% w/w, 0.03 mol) and tetrabutylammonium chloride (0.14 g, 0.005 mol) are then added, at room temperature. The resulting mixture is stirred at 75° C. to 80° C. for 2 hours and 30 minutes. The mixture then is cooled to room temperature, and water (10 mL) is added to the stirred mixture. The aqueous layer is separated, and the resulting organic solution analyzed for anilinofumarate by gas liquid chromatography. Isolation of the product by removal of the solvent yields 1.25 g of anilinofumarate.

Utilizing the above procedure with various phase transfer catalysts, aqueous bases of refluxing concentrations and solvents gives anilinofumarate as illustrated in Table I.

TABLE I

| Example | Phase transfer Catalyst/(mol %) | Solvent | Temp. °C. | Time | Base (conc) | mols | % Yield anilinofumarate (based on starting diethyl maleate) |
|---|---|---|---|---|---|---|---|
| 3 | Benzyltriethylammonium chloride (5.0) | monochlorobenzene | 75–80 | 2.0 | NaOH (33%) | 0.2 | |
| | | | | | K₂CO₃ | 0.1 | 32 |
| 4 | Tetrabutylammonium chloride (5.0) | monochlorobenzene | 75–80 | 2.5 3.0 | NaOH (33%) | 0.3 | 48 |
| 5 | Benzyltriethylammonium chloride (5.0) | monochlorobenzene | 30–43 then 25–30 | 0.5 3.0 | NaOH (33%) | 0.3 | 32 |
| 6 | Benzyltriethylammonium chloride (5.0) | monochlorobenzene | 25–48 then 25–30 | 0.5 2.5 | NaOH (50%) | 0.3 | 18 |

EXAMPLE 7

Preparation of quinoline-2,3-dicarboxylic acid

Vilsmeier reagent is prepared by adding 4.61 g (0.03 mol) of POCl₃, dropwise, to a solution of 2.19 g (0.03 mol) of dimethylformamide in 12 mL of toluene, while maintaining the temperature at 20° C. to 30° C. The two layers are stirred at 20° C. to 30° C. for 60 minutes and then treated, dropwise, with a solution of 5.26 g (0.02 mol) of diethyl anilinofumarate prepared by the procedure of Example 2 above, in 40 mL of toluene while maintaining the temperature at 20° C. to 30° C. The solution that forms on heating is refluxed for 2 hours, cooled until reflux stops and poured into 60 mL of water. The dark syrupy material that precipitates dissolves, on stirring, at room temperature for 30 minutes. Analysis of the toluene solution by glc indicates a yield of 72%. Evaporation of the diester solution gives an oily low melting solid, which upon recrystallization from isopropyl alcohol gives 4.05 g of tan solid, mp 53°–56° C.

Two phases that are formed from 4.1 g (0.015 mol) of diester in 25 mL of toluene and 16 mL of 15% NaOH are refluxed, with good mixing, for 8 hours. The two phases are cooled to 50° C. and 55° C. and diluted with 20 mL of water. The aqueous phase is separated and added dropwise to 11 mL of 35% H₂SO₄ while keeping the temperature below 40° C. This resulting thick mixture is filtered, and the solid collected and dried overnight at 60° C./30-50 mmHg to yield 3.19 g of quinoline-2,3-dicarboxylic acid.

What is claimed is:
1. A method for the preparation of anilinofumarate, said method comprising: reacting a dichlorosuccinate of formula I

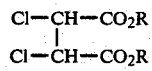

wherein R is C₁-C₄ alkyl, with a molar equivalent of aniline in an inert organic solvent and 2 or greater molar equivalents of an aqueous base in the presence of a phase transfer catalyst at a temperature of about 20° C. to 90° C. for about 1 to 24 hours.

2. A method according to claim 1, wherein said aqueous base is 15% to 50%, on a weight basis, of sodium hydroxide, potassium hydroxide or mixtures thereof.

3. A method according to claim 2, wherein said phase transfer catalyst is a quaternary ammonium salt.

4. A method according to claim 3, wherein said quaternary ammonium salt is tetra-n-butylammonium chloride, benzyltriethylammonium chloride, or mixtures thereof.

5. A method according to claim 4, wherein said organic solvent is a hydrocarbon, aromatic hydrocarbon, chlorinated aromatic hydrocarbon, aromatic hydrocarbon, or mixtures thereof.

6. A method according to claim 5, wherein said solvent is a chlorinated aromatic hydrocarbon, aromatic hydrocarbon, or mixtures thereof.

7. A method according to claim 6, wherein said base is 20% to 50%, on a weight basis, of sodium hydroxide, potassium hydroxide, or mixtures thereof.

8. A method according to claim 7, wherein said base is about 2 to 3 molar equivalents.

9. A method according to claim 8, wherein said temperature is about 20° C. to 85° C.

* * * * *